United States Patent
Launis et al.

(10) Patent No.: US 9,162,108 B1
(45) Date of Patent: Oct. 20, 2015

(54) AUTOMATIC MONITORING AND COACHING OF STRENGTH EXERCISE

(71) Applicant: UNIVERSITY OF JYVÄSKYLÄ, Jyväskylän Yliopisto (FI)

(72) Inventors: Esa Launis, Muurame (FI); Heikki Peltonen, Muurame (FI)

(73) Assignee: UNIVERSITY OF JYVASKYLA, Jyvaskylan Yliopisto (FI)

(*) Notice: Subject to any disclaimer, the term of this patent is extended or adjusted under 35 U.S.C. 154(b) by 0 days.

(21) Appl. No.: 14/308,126

(22) Filed: Jun. 18, 2014

(51) Int. Cl.
| | |
|---|---|
| *A63B 71/00* | (2006.01) |
| *A63B 24/00* | (2006.01) |
| *A63B 21/062* | (2006.01) |
| *A63B 21/00* | (2006.01) |
| *A63B 23/12* | (2006.01) |

(52) U.S. Cl.
CPC ........... *A63B 24/0075* (2013.01); *A63B 21/062* (2013.01); *A63B 21/1469* (2013.01); *A63B 23/1209* (2013.01); *A63B 24/0062* (2013.01); *A63B 71/0054* (2013.01); *A63B 2021/0623* (2013.01); *A63B 2024/0065* (2013.01); *A63B 2024/0068* (2013.01); *A63B 2024/0078* (2013.01)

(58) Field of Classification Search
CPC ........... A63B 24/0075; A63B 24/0062; A63B 21/062; A63B 21/1469; A63B 23/1209; A63B 71/0054; A63B 2021/0623; A63B 2024/0065; A63B 2024/0068; A63B 2024/0078

See application file for complete search history.

(56) References Cited

U.S. PATENT DOCUMENTS

| | | | | |
|---|---|---|---|---|
| 8,348,672 | B2 * | 1/2013 | Saunders | 434/250 |
| 8,747,282 | B2 * | 6/2014 | Lannon et al. | 482/8 |
| 8,812,123 | B2 * | 8/2014 | Carlton et al. | 607/59 |
| 2010/0216600 | A1 | 8/2010 | Noffsinger et al. | |
| 2013/0040271 | A1 * | 2/2013 | Rytky et al. | 434/247 |

FOREIGN PATENT DOCUMENTS

WO   WO 2008/000919 A1   1/2008

\* cited by examiner

*Primary Examiner* — Glenn Richman
(74) *Attorney, Agent, or Firm* — Oliff PLC

(57) ABSTRACT

A data processor maintains an electronic exercise program, which defines exercise sessions defining exercise sets for a subject on one or more exercise apparatuses. The data processor makes a selection (306) between an exercise set (320) and a performance test (308). If a set is selected, instructions relating to the set are given. Each repetition is detected, a risk of injury is assessed, and if a threshold is exceeded, instructions for reducing likelihood for injury are given. Repetitions are counted until detection of a last repetition in the set (410). Feedback is given after the last repetition. If a performance test (308) is selected, instructions relating to the test are given. Subject's performance is monitored until termination of the test. After the test, the exercise program (310) is adapted based on the monitored performance data.

19 Claims, 5 Drawing Sheets

AUTOMATIC MONITORING AND COACHING OF STRENGTH EXERCISE

TECHNICAL FIELD

The present disclosure relates to methods, apparatuses and computer program products for monitoring a subject's exercise in connection with a strength-training equipment.

BACKGROUND

When a person ("subject") follows an exercise program in a gym or comparable environment, progress of the subject and compliance with the program is typically monitored manually by the subject or not monitored at all. This has a number of undesirable consequences. For instance, recording of exercises is prone to errors, inaccuracies and omissions. It is also labor-intensive and typically inconsistent among different exercise apparatuses and gyms. US patent application publication 2010/216600 by Kent Noffsinger et al. discloses a strength training apparatus with automatic exercise monitoring. The Noffsinger apparatus suffers from a number of residual problems, however. For instance, since the resistance against which the subject is exercising is generated in an unconventional manner, the Noffsinger apparatus has poor compatibility with other strength training apparatuses, which is why its use may not be usable as evidence for compliance with planned therapies. To a lesser degree, variations among apparatuses of any type make it difficult to monitor the subject's progress with precision. Another problem is that automatic progress monitoring systems do not detect or adapt to situations wherein the subject is more than usually prone to injury. A yet further problem is that automatic progress monitoring systems from different providers are incompatible with each other.

SUMMARY OF THE DISCLOSURE

It is an object of the present disclosure to alleviate one or more of the problems identified above. Specifically, it is an object of the present disclosure to provide methods, equipment and computer program products that provide improvements with regard to one or more of efficiency of exercise, reporting of progress, verification of subject's participation in planned therapy, detection of conditions for increased risk of injury, adapting of exercise program based on the increased risk of injury and/or based on the subject's performance and/or based on the subject's subjective assessment of condition and/or based on input data entered by third parties, such as movements excluded by a doctor or physiotherapist.

Some implementations of the present disclosure can be permanently installed in exercise apparatuses for gyms, hospitals or homes. Other implementations provide a highly portable combination of hardware and software, wherein a portable data processing device, such as a mobile terminal, is used as a data processing device and its user interface, and a resistance-adjustment element, such as a pin configured to divide a weight stack of an exercise apparatus into moving and non-moving portions comprises the required sensors to detect movement of the weights.

An aspect of the present disclosure is a method comprising:
under control of a programmed data processing device, performing the following acts:
    maintaining an electronic exercise program, the exercise program defining a plurality of exercise sessions, each exercise session defining one or more exercise sets to be performed by a subject on one or more exercise apparatuses;
    for each of several exercise sessions:
    receiving a set of initial subject-related parameters;
    making a selection between an exercise set and a performance test;
    in response to the selection indicating an exercise set, performing the acts of:
        outputting instructions relating to the exercise set;
    for each of several repetitions:
        detecting the repetition;
        counting a number of the repetitions performed in the exercise set until detection of a last repetition in the exercise set;
        after the last repetition in the exercise set, outputting feedback from the exercise set for the subject;
    in response to the selection indicating a performance test, performing the acts of:
        outputting instructions relating to the performance test;
        monitoring performance data relating to the subject's performance on the one or more exercise apparatuses until termination of the performance test;
        after the performance test, adapting the exercise program based on the monitored performance data.

Another aspect of the present disclosure is a data processing device configured to carry out the above method.

Yet another aspect is a tangible program carrier comprising program code instructions whose execution in a data processing device instructs the data processing device to carry out the above method.

A specific embodiment of the invention comprises assessing a risk of injury with respect to one or more risk conditions, each risk condition being associated with likelihood for injury exceeding a predetermined threshold, and in response to detection of one or more risk conditions, outputting instructions for reducing the likelihood for injury.

In some embodiments, detecting the repetition comprises detecting multiple phases of the repetition, wherein the multiple phases are defined by positive and negative changes in potential energy loaded into a current exercise apparatus by the subject. In some embodiments, the multiple phases comprise minimum, increase, maximum and decrease of potential energy stored in the exercise apparatus.

In some embodiments, detecting the repetition may be based on a combination of inputs from a resistance sensor and an acceleration sensor, both of which are attached to a moving portion of a weight stack of the exercise apparatus. The resistance sensor and acceleration sensor may be integrated to a weight-adjustment element configured to divide the weight stack into a moving portion and a non-moving portion.

Adapting the exercise program may comprise adapting one or more of the following parameters: the outputted instructions for the exercise set; planned number of exercise sets in the exercise session; planned weight for the exercise set; planned number of repetitions for the exercise set; planned recovery time for the exercise set; planned number and/or order of the exercise apparatuses involved in the exercise session; and/or planned number and schedule of exercise sessions.

TERMS

Some terms used in the present document will be defined in the following.

Exercise refers to an activity by a subject, wherein one or more muscle groups of the subject are stressed. Objects of the exercise may include increasing, maintaining or assessing (measuring and recording) the subject's performance.

An exercise session is a time during which the subject's exercise activity is interrupted only briefly, such as for brief recovery periods or for movement between exercise apparatuses. Typically, but non-restrictively, an exercise session begins when the subject enters a gym, and ends when the subject leaves the gym.

Exercise apparatus refers to a weight-training apparatus in the present document.

Exercise set is a plurality of repetitions, the number of which is determined by planning or the subject's performance.

Exercise program. Defines a number of exercise sessions, each exercise session defining a number of exercise sets and recovery times between the sets. A data structure underlying the exercise program may be used to record the completed exercise sets and sessions, as well as the subject's measured performance.

Recovery time is the time between exercise activities, such as exercise sets.

A repetition is a periodic unit of exercise, wherein consecutive repetitions differ from each other only by minor variations, fatigue, or the like. A repetition consists of multiple phases and multiple repetitions form an exercise set.

As regards phase of repetition, this document identifies four phases for each repetition, which are defined based on the potential energy of the weight stack. In the present context, words like "up(wards)" or "down(wards)" refer to the position or movement of the weight stack, which may be opposite to the position or movement of the member by which the subject moves the weights, such as a handlebar.

Down-phase of repetition refers to a phase wherein the potential energy of the weight stack reaches its minimum within a repetition.

Upwards-phase of repetition refers to a phase wherein the potential energy of the weight stack increases because the physical force exerted by the subject overcomes the resistance of the exercise apparatus and the weight moves away from the down position.

Up-phase of repetition refers to a phase wherein the potential energy of the weight stack reaches its maximum within a repetition.

Downwards-phase of repetition refers to a phase wherein the potential energy of the weight stack decreases because the resistance of the exercise apparatus overcomes the physical force exerted by the subject and the weight moves towards the down position.

Resistance refers to a force that resists work performed by the subject's muscles. In this document, a static resistance means a resistance that completely overcomes the force exerted by the subject, and the weight stack remains stationary. A dynamic resistance means a resistance lower than the force exerted by the subject, and the weight stack is in motion.

BRIEF DESCRIPTION OF THE DRAWINGS

In the following section, specific embodiments of the disclosure will be described in greater detail in connection with illustrative but non-restrictive examples. A reference is made to the following drawings.

DETAILED DESCRIPTION OF SOME SPECIFIC EMBODIMENTS

Figure 1:
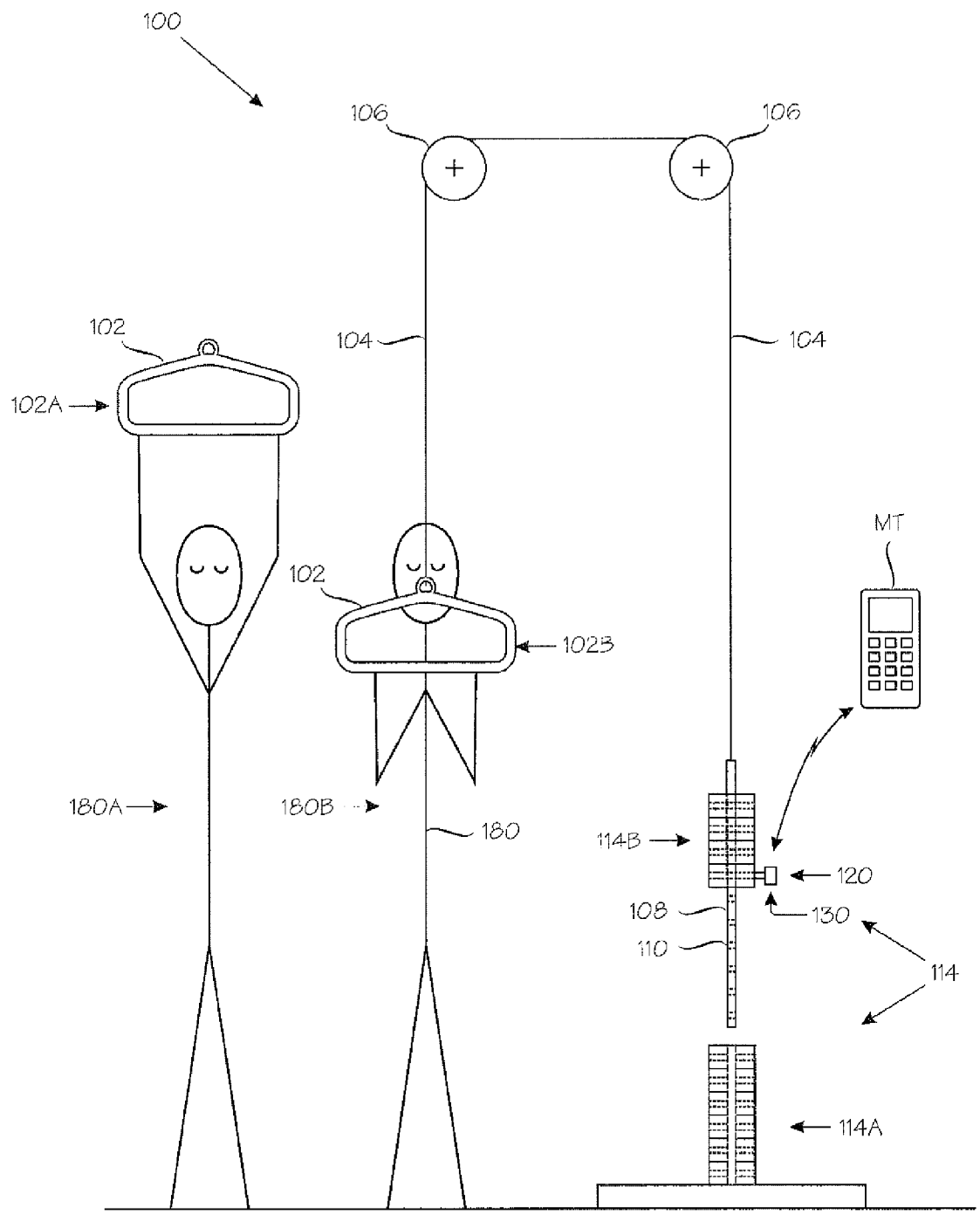
FIG. 1 is a schematic diagram illustrating an exemplary weight-training apparatus.

FIG. 1 is a schematic diagram illustrating an exemplary weight-training apparatus. Reference number 100 generally denotes the weight-training apparatus. Reference number 102 denotes a member by which a subject (user) 180 applies force to the apparatus 100. In the present example, the member 102 is a handlebar, but depending on the muscle group to be trained, the member 102 can forms any of a variety of forms. For instance, the member is frequently arranged as a pivotal member. Reference number 104 denotes a wire or cable by which the force applied by the subject is conveyed over a set of pulleys 106 to a bar 108. The bar 108 has a number of attachment points 110, which in this example are holes. The attachment points 110, eg holes, cooperate with a matching attachment device 120, which in this example, is a movable pin, to move a selectable portion of a weight stack 114 when the subject 180 pulls the member 102. In the scenario shown in FIG. 1, the attachment device (pin) 120 is set to move four of the ten weights of the weight stack 114. The attachment device (pin) 120 thus acts as a resistance-adjustment element, which determines the portion of the weight stack that resists the force applied by the subject.

Reference numbers 114A and 114B denote the portions of the weight stack that remain stationary and move, respectively, when the when the subject 180 pulls the member 102 by a force, which exceeds the weight of the moving portion of the weight stack 114B. Reference numbers 180A and 180B denote the subject in positions wherein the moving portion of the weight stack 114B is down or up, respectively.

Up to this point, the description of the apparatus 100 is well known in the art. In addition to conventional features, the apparatus 100 comprises an electronic controller for automatically monitoring the subject's exercise and for communicating data about the monitored exercise to a mobile terminal MT operated by the subject. In the present example, the controller is denoted by reference number 130 and is placed in the attachment device (pin) 120. The controller 130 comprises a set of sensors and one or more transmitters for conveying the output of the sensors the subject's mobile terminal MT. In addition to sensor data from the controller 130, which detects power applied to the weight stack 114 by the subject 190, the mobile terminal MT may receive sensor data from other sources, such as a heart rate monitor worn by the subject 190 (not shown separately). An example of such a controller 130 is disclosed in EP 2040807 assigned to University of Jyväskylä.

Figure 2:
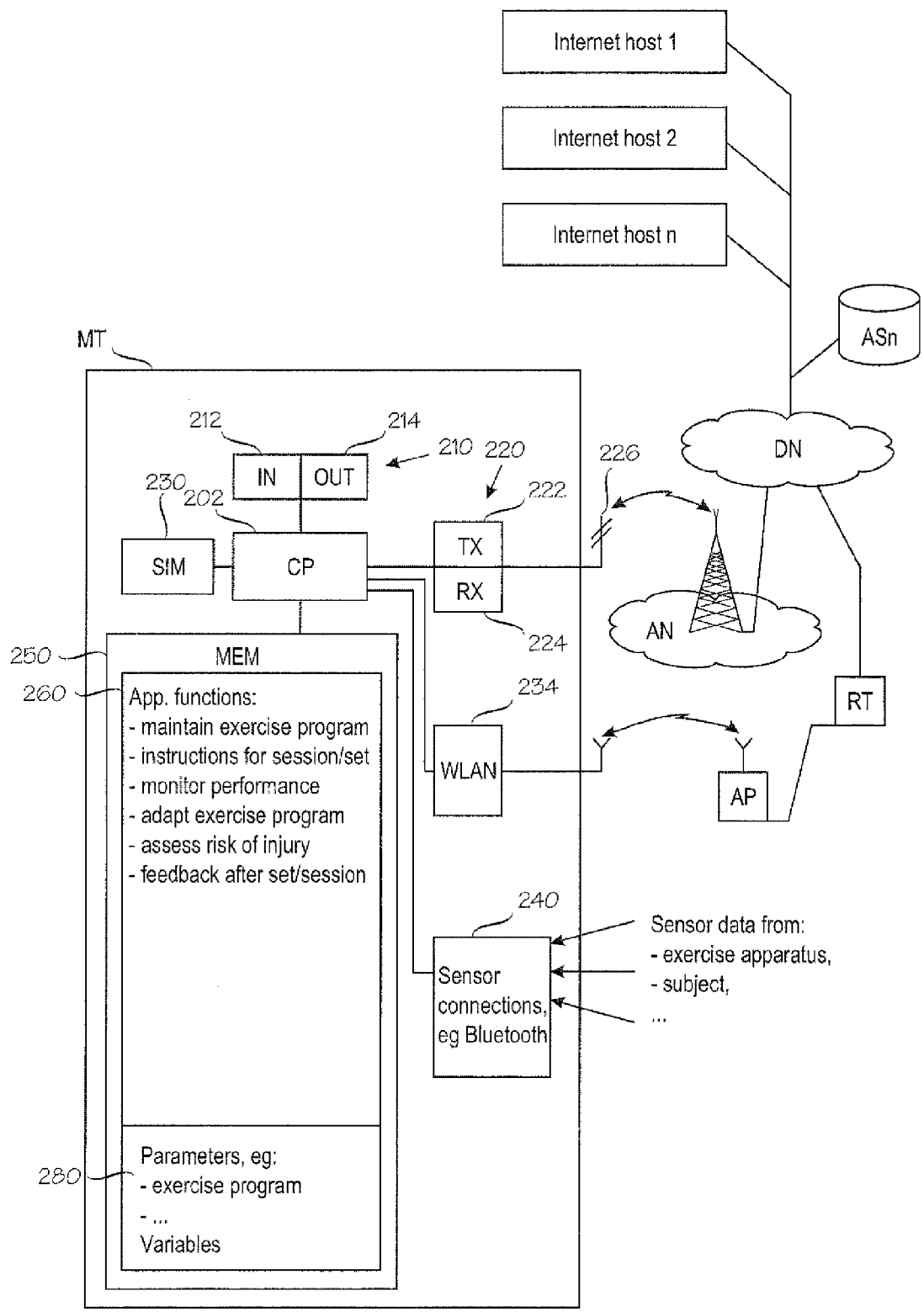
FIG. 2 shows a schematic block diagram of a mobile terminal, which represents an illustrative but non-restrictive implementation of a data processing device adapted to perform the data processing functions relating to the present disclosure.

FIG. 2 shows a schematic block diagram of a mobile terminal. The mobile terminal MT comprises a processing system 202 with at least one central processing unit. The mobile terminal further comprises a memory system 250, which typically comprises a combination of fast volatile memory and slower nonvolatile memory, as is well known to those skilled in the art. In addition, the mobile terminal MT comprises or utilizes a user interface 210, which comprises an input circuitry 212 and an output circuitry 214. The input circuitry 212 comprises the mobile terminal's microphone and user-input devices, such as a keypad and/or touch screen. The output circuitry 214 comprises the mobile terminal's display, earphone, loudspeaker and/or vibrator. The mobile terminal MT further comprises reception/transmission circuitry 220 which comprises a transmission circuitry 222, reception circuitry 224 and antenna 226. A subscriber identity module, SIM, 230 is used by an authentication function to authenticate the mobile terminal's user and to identify the user's subscription to the access network AN. A typical mobile terminal also comprises WLAN (Wireless Local Area Network) circuitry 234 whose normal mode of usage is acting as a WLAN client to a WLAN access point AP and a router RT.

In order to support installable program modules, the mobile terminal's memory 250 typically comprises routines for downloading installable program modules and for storing the installable program modules as apps (applications) 260 in the memory 250 for execution by the central processing unit CP. FIG. 2 shows an arrangement in which the mobile terminal is configured to download installable program modules from an app store ASn (n=1, 2, 3, . . . , depending on the platform) via a data network DN, an access network AN, the antenna 226 and reception circuitry 224. Instead of downloading software from the app store over the access network, or in addition to it, other arrangements are equally possible, such as downloading the installable program modules via the data network DN to a separate data terminal (not shown), from which the installable program modules are transferred to the mobile terminal via the WLAN circuitry 234 or via some other short-range connection, such as Bluetooth or Universal Serial Bus (USB, not shown separately). The access network AN is typically a broadband-capable mobile communication network, while the data network DN is typically the internet or some closed subnetwork implementing internet protocol (IP), commonly called intranets or extranets. At this level of generalization, all previously-discussed elements of FIG. 2 can be conventional as used in the relevant art. One or more external hosts are accessible via the access network AN and data network DN, as will be described in more detail below.

Reference number 240 denotes a connection, such as Bluetooth connection, to external sensors, by which the mobile terminal MT receives exercise-related data from the exercise apparatus 100. Typically, such sensor data indicates the weight 114B moved by the subject 190, the length of the movement, rate and timing of the repetitions and phases of repetition. In addition to sensor data from the exercise apparatus, the sensor data received by the mobile terminal may include heart beat data from an external heart rate monitor, electrocardiogram or other physical measurements.

Reference numeral 280 denotes an area of the memory 250 used to store parameters and temporary variables. Typically the memory area 280 stores an exercise program. For instance, the exercise program may be created by a human coach or physiotherapist, based on the subject's condition, objects, condition-related constraints, and so on. In some embodiments the exercise program may be created automatically.

The exercise program, as stored in the memory area 280 of the mobile terminal, is a data structure, which typically indicates certain exercise-related parameters. The exercise-related parameters may comprise an exercise program, history data from previous exercise sessions and detailed performance data from an ongoing session, if any. The data structure underlying the exercise program can be used to store, not only the planned exercise program, but also measured and recorded performance of the subject. An example of an exercise program will be described in connection with FIG. 5.

Figure 3:
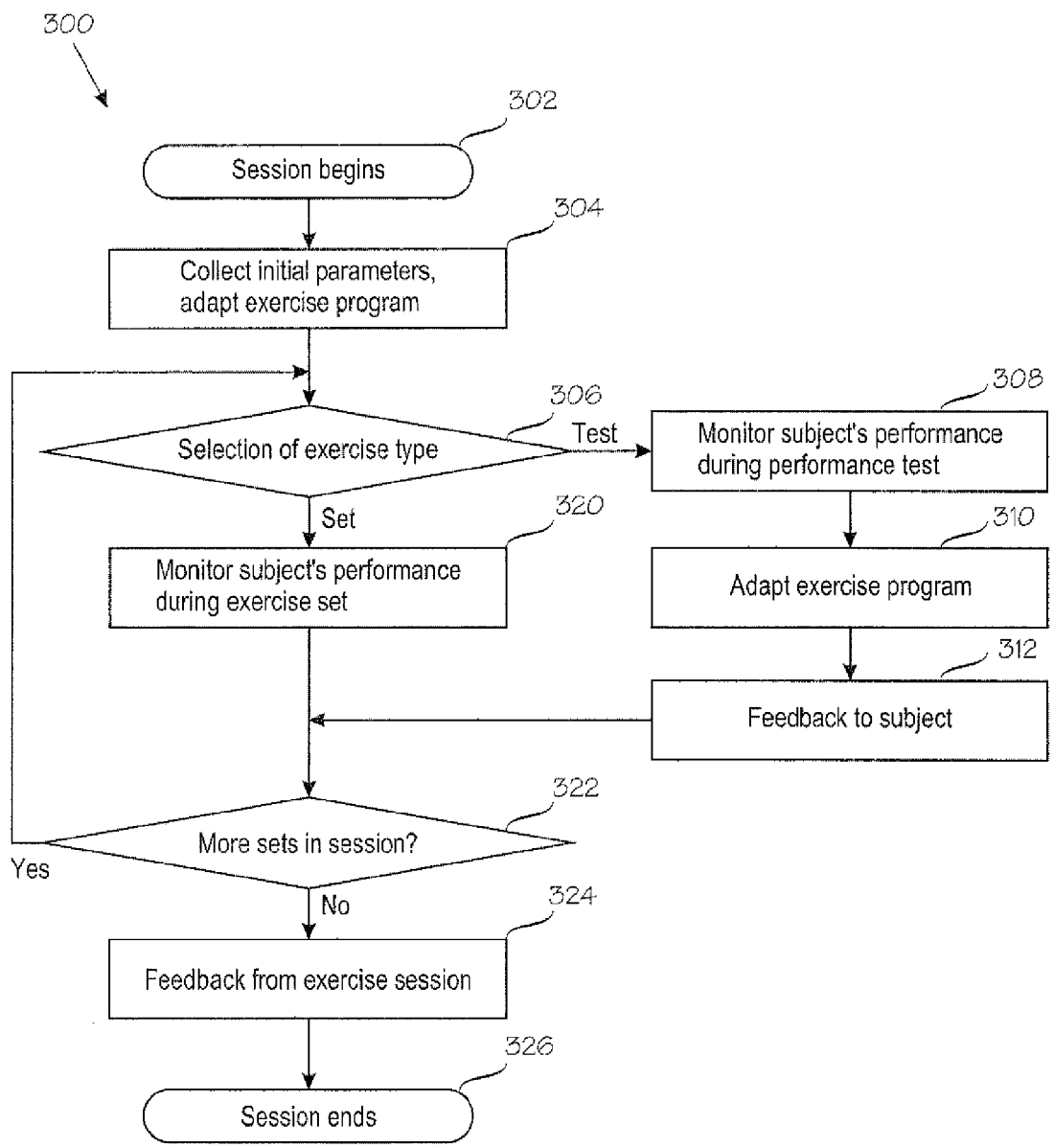
FIG. 3 is a flow chart illustrating general operation of an embodiment of the disclosure.

FIG. 3 is a flow chart illustrating overall operation of a process 300 for monitoring a subject's performance during an exercise session. The process 300 is executed by a data processing device, which typically is the subject's own mobile terminal MT provided with a software application 260 according to an aspect of the present disclosure.

The process begins at step 302. Reference number 304 denotes a step of collecting initial parameters, including a exercise program, the subject's subjective assessment of their current condition and/or energy level. Step 304 optionally comprises assessing input from external actors, such as doctors, physiotherapists, coaches, and so on. In addition, step 304 may comprise assessing the limitations and constraints of the gym the subject is currently exercising in. The exercise program may be adapted according to the collected initial parameters. For instance, the subject may be recovering from illness, injury or treatment. As a result, the numbers of sets, repetitions in each set, and/or the weights used may be lowered. Or, some sets requiring specific motion, such as torsional motion, may be canceled if required by the subject's assessment of their own condition or by instructions from a doctors, physiotherapist or the like.

Step 306 is a selection of exercise type. The options include an exercise set and a performance test. If a performance test is selected, the process continues to step 308, in which the subject's performance is monitored during the test. Some implementations of the disclosure support multiple different performance tests. For instance, one type of performance test involves moving weights, that is, weights whose resistance can be overcome by the force exerted by the subject, at least initially. The performance test may run for a predetermined time, and the number of repetitions performed by the subject is counted. Or, the subject may continue as long as they can perform more repetitions. Another type of performance test involves stationary weights whose resistance overcomes the force exerted by the subject. This type of performance test permits measuring the maximum force exerted by the subject.

Based on the results of the performance test, the exercise program is adapted in step 310. In step 312, the subject is provided with feedback that indicates their progress with respect to exercising. The feedback also includes instructions for future exercises. The process 300 proceeds to step 322, which will be described shortly.

If an exercise set was selected in step 306, the process proceeds to step 320, in which the subject's performance will be monitored during the exercise set. Step 320 will be described in more detail in connection with FIG. 4. After step 320, the process proceeds to step 322.

Step 322 is a test, in which the data processing device checks if the exercise program indicates more exercise sets for the current exercise session. If yes, the process returns to step 304. If there are no more sets in the current session, the process proceeds to step 324, which comprises providing the subject with feedback from the current exercise session. The session ends in step 326.

Figure 4:
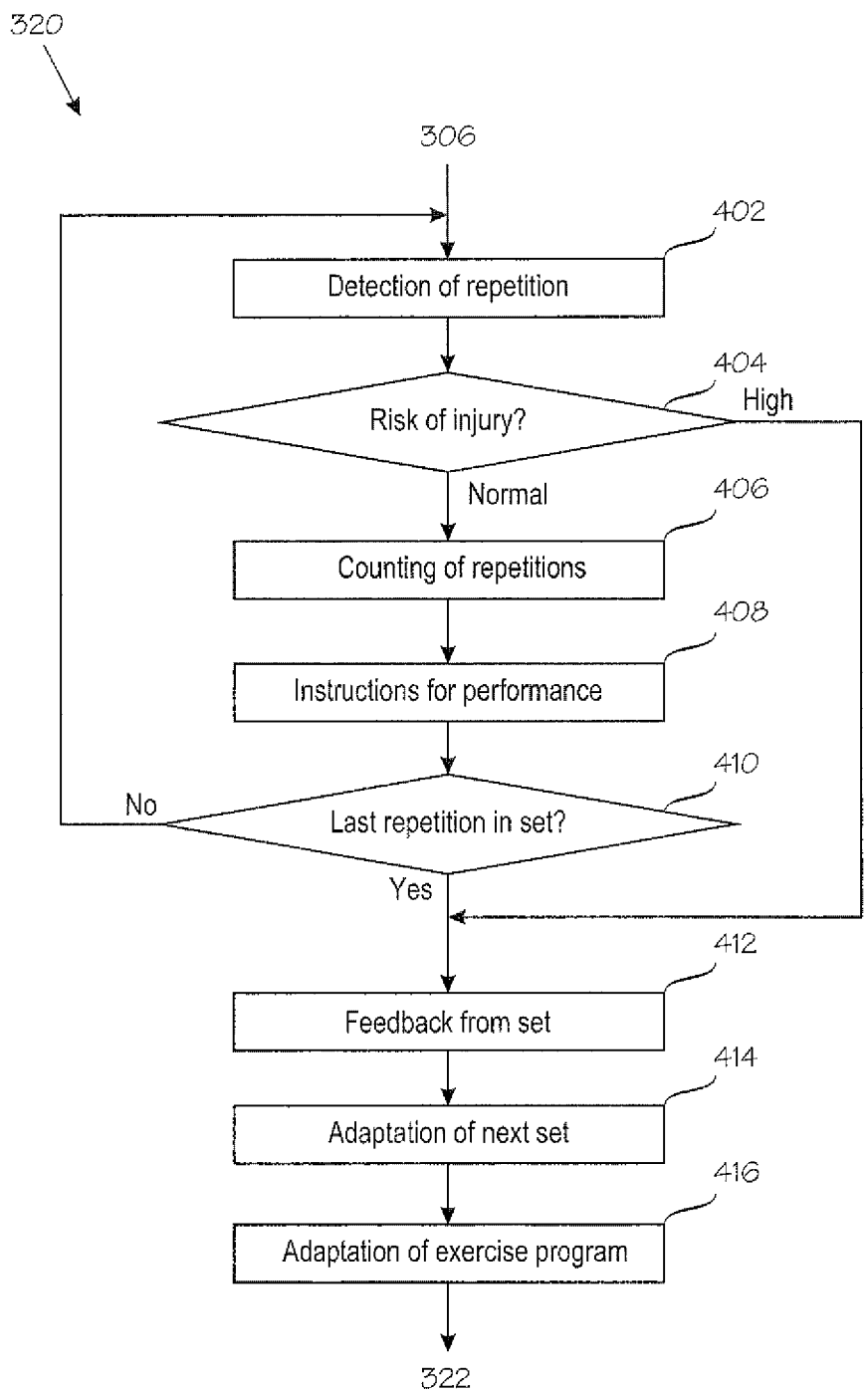
FIG. 4 is a more detailed flow chart illustrating some phases of the flow chart shown in FIG. 3.

FIG. 4 is a more detailed flow chart illustrating step 320 of FIG. 3 in more detail. Step 320, located between steps 306 and 322 in the process 300, is the step in which the subject's performance is monitored during an exercise set. In the implementation shown in FIG. 4, step 320 is divided into even-numbered sub-steps 402, 404, . . . , 416.

Step 402 comprises detection of each repetition. Referring to FIGS. 1 and 2, the software application 260 being executed in the data processing device, such as the subject's mobile terminal MT, uses its sensor connections to collect sensor data from the controller 130 in the exercise apparatus. In an illustrative but non-restrictive implementation, the controller 130 is mounted on a pin 120, which determines the moving portion 114B of the weight stack 114 and moves along with the moving portion. The controller 130 comprises one or more stress sensors for detecting the weight of the moving portion 114B of the weight stack 114. The stress can be measured for example by stretch/shrinkage, bending or pressure. The controller 130 comprises one or more accelerometers for detecting movement of the weights 114B. The controller 130 can be integrated in the pin 120 or in another part of the training apparatus. Naturally, there are alternative techniques for indicating when a repetition begins and ends. For instance, the size of the moving portion of the weight stack and its motion may be detected optically, magnetically, or by means of a variety of proximity detection techniques.

Step 404 comprises assessment of risk of injury. Risk of injury may be assessed, for example, by comparing various repetition-related performance parameters observed in the current set with corresponding parameters observed in previous sets in the current session or previous sessions. For example, the performance parameters used for risk assessment may comprise one or more of the following: repetition rate (duration of a complete repetition), duration of one or more individual phases of a repetition, force production and capacity of the subject and external monitoring data. If an unusually high risk of injury is detected, the process proceeds to steps 412 and 414, which will be described shortly.

If a normal risk level is detected, the process proceeds to step 406, in which the repetitions in the current set are counted. In an illustrative but nonrestrictive implementation, a repetition is counted when the moving portion 114B of the weight stack moves from the down position to the up position. It should be noted that some exercise apparatuses have well-defined limits for movement, and detections of the down position and up position are relatively straightforward. In other exercise apparatuses the movement of the weight stack is not constrained at the down position, the up position or both. For instance, in the apparatus shown in FIG. 1, the subject may first pull the member (handlebar) 102 from a resting position to an initial position 102A. It is the initial position and not the resting position that corresponds to the down position of the weight stack for each repetition. The up position of the weight stack corresponds to the case where the member 102 has been pulled to position 102B. Neither of the positions 102A, 102B is fixed. Instead the positions 102A, 102B depend on the dimensions of the subject. Instead of detecting absolute positions of the weight stack, the software application 260 being executed in the data processing device may use the accelerometer(s) and/or stress sensor(s) of the controller 130. The accelerometers indicate moments when movement changes from up to down or vice versa. The stress sensors indicate moments when the force exerted by the subject decreases as the weight stack approaches the up position.

Step 406 for counting repetitions is preferably adaptive and learns the special force patterns applied by individual subjects. The repetition-counting process may also be capable of recognizing explosive repetitions (those performed as quickly as possible) or repetitions performed slowly (or normally).

Step 408 comprises instructing or coaching the subject. In an illustrative but non-restrictive implementation, the software application 260 may use the display of the data processing device, such as the mobile terminal MT, to display an indication which helps the subject to maintain an optimal pace. For example, the indication may be a shape that wanders off indicated track if the subject deviates from the optimal pace.

Step 410 comprises checking if the current repetition is the last one in the set. Specifically, the software application 260 compares the number of the current repetition with the total number of repetitions in the current set, as indicated by the exercise program. Step 410 is preferably executed during the repetition, whereby an indication may be given to the subject. As a result, the subject is prepared to end the set in a controlled manner, without having to prepare for one more repetition, which is then canceled because the set was completed. In some training programs it might be possible for the users to continue after last indicated repetition. If the current repetition is not the last one in the set, process returns to step 402 after the current repetition.

On the other hand, if the most repetition was the last in the set, process proceeds to step 412, in which the subject is provided with feedback from the set, which was just completed. The feedback comprises performance-related data and, optionally, instructions for ensuring safe and efficient exercising.

Step 414 comprises adapting the next exercise set. If step 414 was preceded by step 412 (feedback from set just completed), the performance-related data may be compared with the subject's previous performance. If the comparison indicates that the subject is performing significantly below their normal level, the next set may be adapted to be less demanding than normally. Conversely, if the subject is performing significantly above their normal level, the next set may be adapted to be more demanding than normally. On the other hand, if step 414 was preceded by step 404 (assessment of risk of injury), one or more sets may be made less demanding, may be replaced by other types of exercise, or may be canceled altogether or added to the current session.

Finally, step 416 comprises adaptation of the exercise program according to the results of the set just completed. Adaptation of the exercise program may comprise changing the parameters of one or more sets. For instance, the changed parameters may relate to numbers of repetitions in each set, weights used, repetition rate, recovery times. Alternatively or additionally, exercise sets may be canceled or replaced with more or less demanding ones or new exercise sets can be added. Those skilled in the art will realize that adaptation of the next set and/or the exercise program may alternatively or additionally take place in the process shown in FIG. 3, for instance immediately before or after the step 324 of providing feedback.

Figure 5:
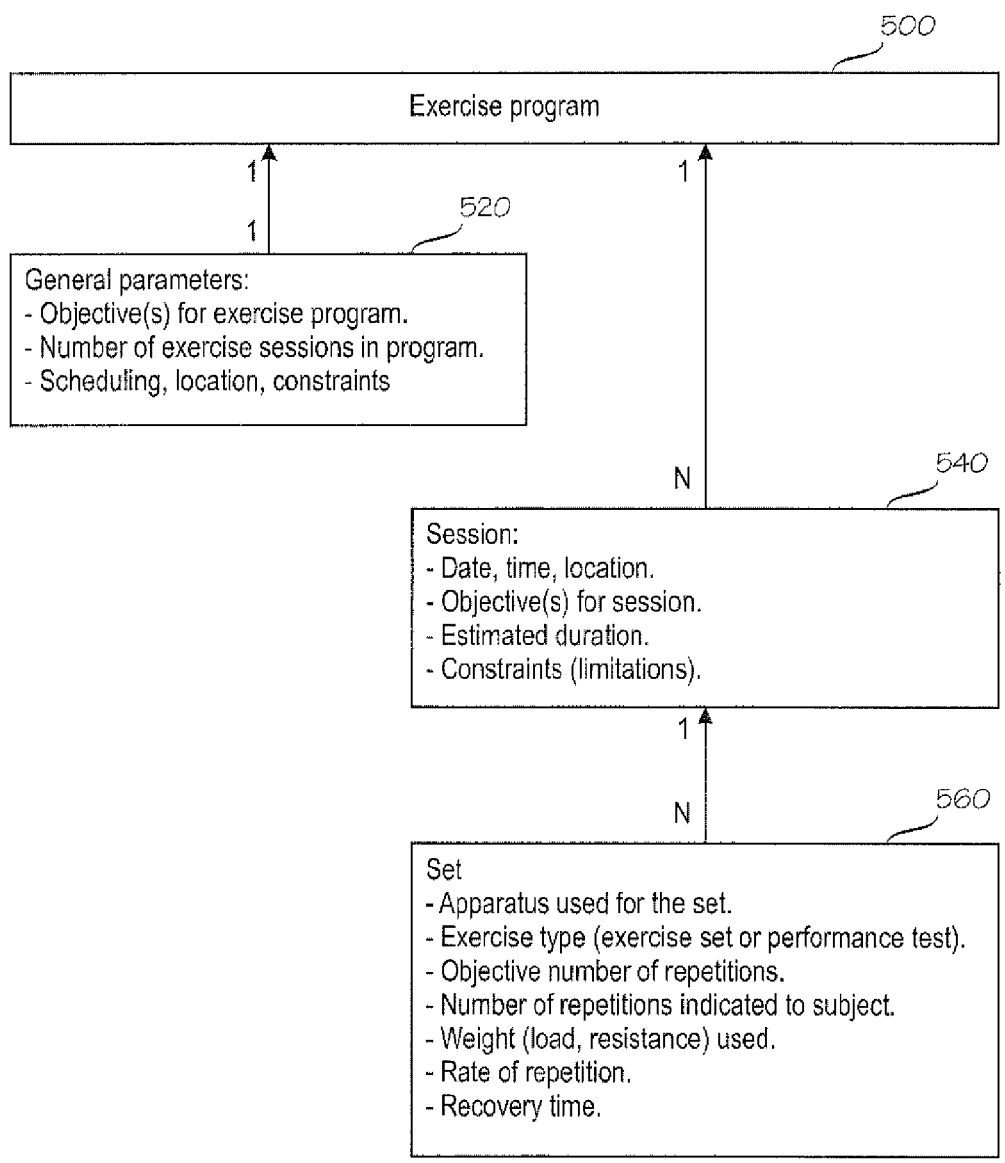
FIG. 5 illustrates data structures relating to an exercise program.

FIG. 5 illustrates data structures relating to an exercise program 500, The exercise program 500 comprises a set of general parameters, generally denoted by reference number 520. The general parameters 520 may comprise the following parameters for the overall exercise program:

One or more objectives for the exercise program. Non-limiting examples of the objectives include: increase of muscular mass, increase of maximum strength, weight loss for the subject. An objective may also indicate a group of target muscles, such as leg muscles.

Number of exercise sessions in the planned exercise program.

Scheduling of exercise sessions. Input parameters for the scheduling include the number of exercise sessions per unit of time (eg a week), suitable dates and times for the subject and gym.

Principal location of exercise and its apparatus-related constraints and limitations.

In addition to the general parameters 520, the exercise program 500 typically comprises a definition 540 for each of several exercise sessions. In the present illustrative example, the definition 540 for an exercise session comprises:

Planned or realized date, time and location for the session.

One or more objectives for the exercise session. The objectives for an individual exercise session are typically indicated with more detail than the objectives for the overall program. For instance, although the subject's weight loss may be included as an overall object in the exercise program, there may be individual exercise sessions whose objectives do not include weight loss.

Estimated duration. The duration can be estimated based on the number and duration of individual exercise sets and the recovery times between them.

Constraints (limitations). For instance, apparatus-related constraints may be caused by lack of a suitable exercise apparatus. Subject-related constraints may be caused by the subject's condition. For instance, the subject may not be able to withstand forces, movement ranges or types exceeding a set limit in connection with certain muscles, muscle groups and/or joints.

Each definition 540 for an exercise session comprises at least one, and typically definitions 560 for exercise sets. In the present illustrative example, the definition 560 for each exercise set comprises:

The exercise apparatus on which the exercise is to be done.

Exercise type (exercise set or condition testing).

Objective (actual) number of repetitions required from the subject.

Number of repetitions indicated to the subject. These two numbers may differ in cases where it is desired that the subject exercises all the way to a fatigue condition. For instance, if the objective number of repetitions in a set is estimated to be 8-10, all the way until interrupted because of excessive fatigue, the subject may be requested to perform 12 repetitions as quickly as possible.

Weight (load, resistance),

Rate of repetition. May be indicated as repetitions per unit of time, or "as quickly as possible".

Recovery time between two consecutive exercise sets.

Those skilled in the art will realize that the inventive principle may be modified in various ways without departing from the spirit and scope of the present disclosure.

The invention claimed is:

1. A method comprising:
under control of a programmed data processing device, performing the following acts:
maintaining an electronic exercise program, the exercise program defining a plurality of exercise sessions, each exercise session defining one or more exercise sets to be performed by a subject on one or more exercise apparatuses;
for each of several exercise sessions:
receiving a set of initial subject-related parameters;
making a selection between an exercise set and a performance test;
in response to the selection indicating an exercise set, performing the acts of:
outputting instructions relating to the exercise set;
for each of several repetitions:
detecting the repetition;
counting a number of the repetitions performed in the exercise set until detection of a last repetition in the exercise set;
after the last repetition in the exercise set, outputting feedback from the exercise set for the subject;
in response to the selection indicating a performance test, performing the acts of:
outputting instructions relating to the performance test;
monitoring performance data relating to the subject's performance on the one or more exercise apparatuses until termination of the performance test;
after the performance test, adapting the exercise program based on the monitored performance data.

2. The method according to claim 1, further comprising assessing a risk of injury with respect to one or more risk conditions, each risk condition being associated with likelihood for injury exceeding a predetermined threshold, and in response to detection of one or more risk conditions, outputting instructions for reducing the likelihood for injury.

3. The method according to claim 1, wherein detecting the repetition comprises detecting multiple phases of the repetition, wherein the multiple phases are defined by positive and negative changes in potential energy loaded into a current exercise apparatus by the subject.

4. The method according to claim 3, wherein the multiple phases comprise minimum, increase, maximum and decrease of potential energy stored in the exercise apparatus.

5. The method according to claim 1, wherein detecting the repetition is based on a combination of inputs from a resistance sensor and an acceleration sensor, both of which are attached to a moving portion of a weight stack of the exercise apparatus.

6. The method according to claim 5, wherein the resistance sensor and acceleration sensor are integrated to a weight-adjustment element configured to divide the weight stack into a moving portion and a non-moving portion.

7. The method according to claim 3, further comprising outputting instructions related to timing of the multiple phases during the repetition.

8. The method according to claim 1, wherein adapting the exercise program comprises adapting one or more of the following parameters:
the outputted instructions for the exercise set;
planned number of exercise sets in the exercise session;
planned weight for the exercise set;
planned number of repetitions for the exercise set;
planned recovery time for the exercise set;
planned number and/or order of the exercise apparatuses involved in the exercise session;
planned number and schedule of exercise sessions.

9. The method according to claim 1, wherein the data processing device is a mobile terminal provided with an installable software application.

10. A programmed data processing device, comprising:
a memory system for storing program code instructions and data;
a processing system comprising at least one processing unit, wherein the processing system is configured to execute at least some of the program code instructions and to process the data stored in the memory system;
a sensor connection system for receiving sensor data from an exercise apparatus;
wherein the memory system comprises at least one application, when executed by the processing system, causes the processing system to perform the acts of:
maintaining an electronic exercise program, the exercise program defining a plurality of exercise sessions, each exercise session defining one or more exercise sets to be performed by a subject on one or more exercise apparatuses;

for each of several exercise sessions:

receiving a set of initial subject-related parameters;

making a selection between an exercise set and a performance test;

in response to the selection indicating an exercise set, performing the acts of:

outputting instructions relating to the exercise set;

for each of several repetitions:

detecting the repetition;

counting a number of the repetitions performed in the exercise set until detection of a last repetition in the exercise set;

after the last repetition in the exercise set, outputting feedback from the exercise set for the subject;

in response to the selection indicating a performance test, performing the acts of:

outputting instructions relating to the performance test;

monitoring performance data relating to the subject's performance on the one or more exercise apparatuses until termination of the performance test;

after the performance test, adapting the exercise program based on the monitored performance data.

11. The programmed data processing device according to claim 10, wherein the at least one application, when executed by the processing system, further causes the processing system to assess a risk of injury with respect to one or more risk conditions, each risk condition being associated with likelihood for injury exceeding a predetermined threshold, and in response to detection of one or more risk conditions, to output instructions for reducing the likelihood for injury.

12. The programmed data processing device according to claim 10, wherein detecting the repetition comprises detecting multiple phases of the repetition, wherein the multiple phases are defined by positive and negative changes in potential energy loaded into a current exercise apparatus by the subject.

13. The programmed data processing device according to claim 12, wherein the multiple phases comprise minimum, increase, maximum and decrease of potential energy stored in the exercise apparatus.

14. The programmed data processing device according to claim 10, wherein detecting the repetition is based on a combination of inputs from a resistance sensor and an acceleration sensor, both of which are attached to a moving portion of a weight stack of the exercise apparatus.

15. The programmed data processing device according to claim 14, wherein the resistance sensor and acceleration sensor are integrated to a weight-adjustment element configured to divide the weight stack into a moving portion and a non-moving portion.

16. The programmed data processing device according to claim 12, further comprising outputting instructions related to timing of the multiple phases during the repetition.

17. The programmed data processing device according to claim 10, wherein adapting the exercise program comprises adapting one or more of the following parameters:

the outputted instructions for the exercise set;

planned number of exercise sets in the exercise session;

planned weight for the exercise set;

planned number of repetitions for the exercise set;

planned recovery time for the exercise set;

planned number and/or order of the exercise apparatuses involved in the exercise session;

planned number and schedule of exercise sessions.

18. The programmed data processing device according to claim 10, wherein the data processing device is a mobile terminal provided with an installable software application.

19. A tangible program carrier comprising program code instructions for a data processing device, which comprises a memory system for storing program code instructions and data;

a processing system comprising at least one processing unit, wherein the processing system is configured to execute at least some of the program code instructions and to process the data stored in the memory system;

a sensor connection system for receiving sensor data from an exercise apparatus;

wherein the program code instructions, when executed by the processing system, causes the processing system to perform the acts of:

maintaining an electronic exercise program, the exercise program defining a plurality of exercise sessions, each exercise session defining one or more exercise sets to be performed by a subject on one or more exercise apparatuses;

for each of several exercise sessions:

receiving a set of initial subject-related parameters;

making a selection between an exercise set and a performance test;

in response to the selection indicating an exercise set, performing the acts of:

outputting instructions relating to the exercise set;

for each of several repetitions:

detecting the repetition;

counting a number of the repetitions performed in the exercise set until detection of a last repetition in the exercise set;

after the last repetition in the exercise set, outputting feedback from the exercise set for the subject;

in response to the selection indicating a performance test, performing the acts of:

outputting instructions relating to the performance test;

monitoring performance data relating to the subject's performance on the one or more exercise apparatuses until termination of the performance test;

after the performance test, adapting the exercise program based on the monitored performance data.

* * * * *